US005371483A

United States Patent [19]

[11] Patent Number: 5,371,483

Bhardwaj

[45] Date of Patent: Dec. 6, 1994

[54] HIGH INTENSITY GUIDED ULTRASOUND SOURCE

[76] Inventor: Mahesh C. Bhardwaj, 238 E. Doris Ave., State College, Pa. 16801

[21] Appl. No.: 170,032

[22] Filed: Dec. 20, 1993

[51] Int. Cl.[5] .......... A61B 8/12; H03H 9/30

[52] U.S. Cl. .......... 333/149; 128/662.03; 128/662.06; 128/663.01

[58] Field of Search .......... 128/662.03, 662.06, 128/663.01; 333/149, 150, 154, 254; 367/140; 381/154; 385/7, 13, 40, 88; 310/327, 335, 338, 369, 371

[56] References Cited

U.S. PATENT DOCUMENTS

| | | | |
|---|---|---|---|
| 3,663,842 | 5/1972 | Miller | 310/8.3 |
| 4,184,094 | 1/1980 | Kopel | 310/335 |
| 4,764,905 | 8/1988 | Granz et al. | 367/140 |
| 5,042,492 | 8/1991 | Dubut | 128/662.03 |
| 5,094,108 | 3/1992 | Kim et al. | 73/627 |
| 5,111,805 | 5/1992 | Jaggy et al. | 128/24 |
| 5,127,410 | 7/1992 | King et al. | 128/662.03 |
| 5,193,527 | 3/1993 | Schafer | 128/24 |
| 5,212,671 | 5/1993 | Fujii et al. | 367/151 |
| 5,217,018 | 6/1993 | Dias | 128/662.06 |
| 5,284,148 | 2/1994 | Dias et al. | 128/662.06 |
| 5,289,436 | 2/1994 | Terhune | 381/154 |

*Primary Examiner*—George Manuel
*Attorney, Agent, or Firm*—Webb Ziesenheim Bruening Logsdon Orkin & Hanson

[57] ABSTRACT

An ultrasound source for transmitting ultrasound along a fiber or rod comprises a thin piezoelectric element having two closely spaced apart concave and convex surfaces and an acoustic intensifier abutting the concave surface. The acoustic intensifier tapers from the concave surface to a narrow cross section. A cylindrical fiber or rod extends from the acoustic intensifier at the narrow cross section.

11 Claims, 1 Drawing Sheet

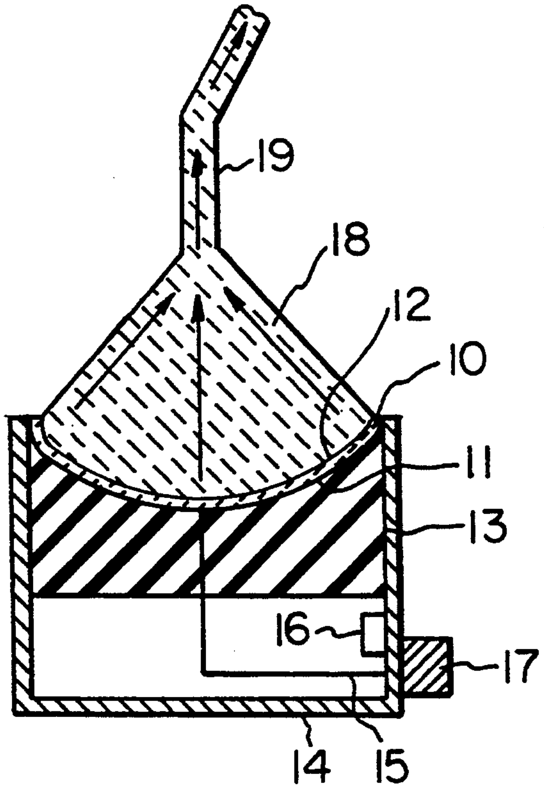
19
18
12
10
11
13
16
17
14
15

HIGH INTENSITY GUIDED ULTRASOUND SOURCE

FIELD OF THE INVENTION

This invention is related to ultrasound sources or transducers.

BACKGROUND OF THE INVENTION

In the characterization of parts or materials with ultrasound, it is often necessary to keep the ultrasound transducer spaced away from the materials. This is especially the case when the parts or materials are at high temperatures or subject to corrosive chemical conditions.

In the medical arts, ultrasound is used for diagnosis and for treatment of conditions such as malignant tissues, particularly in restricted locations in the body. Treatment may involve the ablation of malignant tissue. The transducer size, if used in the arterial or vascular system, must have a size to match the interiors of the blood vessels.

Reducing the size of transducers presents two major problems. First, the intensity of the ultrasound is reduced by the small transducer size. Second, the small parts may be fragile offering the possibility of disintegration in the body.

It is an advantage, according to this invention, to provide an ultrasound source that has sound intensity and signal quality enabling accurate measurement of parts or material properties.

It is a further advantage of this invention to provide an ultrasound source that can safely be used in the medical arts in confined spaces such as blood vessels.

SUMMARY OF THE INVENTION

Briefly, according to this invention, there is provided an ultrasound source wherein the ultrasound is transmitted along a fiber or rod and out the distal end thereof. The source comprises a thin piezoelectric element having two closely spaced apart surfaces and having electrodes on each face. By applying a voltage pulse across the two electrodes, the piezoelectric element is excited to vibrate and emit a pulse of ultrasound at frequencies related to the piezoelectric material and the thickness of the element. One face of the piezoelectric element is a concave surface and the other face is a convex surface. A damping substrate abuts the convex surface. An acoustic intensifier abuts the concave surface. The acoustic intensifier tapers from the concave surface to a narrow cross section. It may, for example, be a cone or a truncated pyramid. (A pyramid is a polyhedron having for its base a polygon and for its other faces, triangles with a common apex.) A cylindrical fiber or rod extends from the acoustic intensifier at the narrow cross section. The rod may be circular cylindrical of have other cross-sectional shapes such as a square or a rectangle. It may be formed integrally with the acoustic intensifier or it may be joined thereto ill intimate abutting relationship. The smallest distance across any section of the cylindrical fiber or rod is greater than one and less than five wavelengths of the ultrasound generated by the piezoelectric element. The shapes and sizes of the intensifier and cylindrical fiber or rod are such that they meet in the vicinity where the ultrasound vibrations converge on an area which is preferably slightly smaller than the narrow cross section. The width of the fiber or rod should be slightly larger than the ultrasound beam size at its focal point.

Preferably, the focal length of the piezoelectric element resulting from its concave surface in contact with the intensifier is between about R and about $D^2/4\lambda$ where R is the radius of curvature of the concave surface of the piezoelectric element near its geometric center, D is the average length across the concave surface of the piezoelectric element and $\lambda$ is the wavelength of the ultrasound generated by the piezoelectric element. Preferably, the concave surface has a circular edge. It is also preferred that the radius of curvature of the concave surface does not vary more than about 20 percent over the entire surface.

It is most preferred that the intensifier occupies a solid angle between $\pi$ and $\pi/2$ steradians. In this way, the surface area of the piezoelectric element can be increased relative to the narrow cross section of the intensifier while reducing the distance from the surface to the narrow cross section. The upper limit on the size of the solid angle is based upon minimizing the angle of entry of the sound waves into the rod or fiber. Another way of stating this condition is that the angle between a line on the tapered surface of the intensifier and the axis of the fiber or rod is between about $\pi/3$ and $\pi/6$ radians.

In a preferred embodiment, according to this invention, the concave surface of the piezoelectric element is substantially spherical and has a substantially circular edge and the acoustical intensifier has a conical surface tapering from the circular edge to the narrow cross section from which a circular cylindrical fiber or rod extends. The focal length of the piezoelectric element and intensifier is between about R and about $D^2/4\lambda$ where R is the radius of curvature of the concave surface of the piezoelectric element, D is the diameter of the circular edge of the concave surface of the piezoelectric element and $\lambda$ is the wavelength of the ultrasound generated by the piezoelectric element. The diameter of the circular cylindrical fiber or rod is between one and three times the wavelength of the ultrasound generated by the piezoelectric element.

In yet another preferred embodiment, the concave surface of the intensifier is a parabolic surface.

Depending upon the materials from which the intensifier and fiber or rod are made and the atmosphere or fluids that contact the surfaces thereof during use, it may be desirable to provide the intensifier and the fiber or rod with a sound reflective coating.

THE DRAWING

Further features and other objects and advantages of this invention will become clear from the following detailed description made with reference to the drawing in which:

The drawing is a section view through an ultrasound source according to this invention.

DESCRIPTION OF THE PREFERRED EMBODIMENTS

Whereas it is possible to launch ultrasound through fibers or rods by placing an end thereof on a flat or planar piezoelectric material, experience has shown that this approach does not produce high intensity and high signal quality bulk waves simultaneously (particularly in the case of fibers). In this invention, the problem has been solved by placing a shaped ultrasound intensifier on a geometrically focused piezoelectric element. By placing a suitable fiber or rod at the end of the intensifier or by making the rod or fiber an integral part of the intensifier, very high density bulk waves are propagated through the fiber or rod.

Referring to the drawing, the piezoelectric element 10 has a curved shape defining convex and concave faces. Conductive coatings on each face comprise electrodes 11 and 12. The composition of the piezoelectric element may comprise lead zirconate-lead titanate (PZT), lead meta-niobate (PMN), polyvinyline difluoride (PVDF), composite PZTs, PMNs and other materials characterized by the phenomenon of piezoelectricity.

Abutting the electrode on the convex side of the piezoelectric element is a damping substrate 13 for controlling the pulse shape and power. This substrate may comprise ceramic materials, epoxies or rubber materials, singly or mixed with ceramic and metal powders and other known suitable materials.

The piezoelectric element 10 and the substrate 13 are mounted in case 14, here shown as a metal case. A socket 17 for a coaxial cable is mounted in the case 14. Lead 15 and ground lead 16 connect the socket to the electrodes 11 and 12, respectively.

An ultrasound intensifier 18 abuts the ground electrode 12 and tapers to a narrow cross section where it joins a fiber or rod 19. The intensifier with fiber or rod can be made from various materials that transmit ultrasound efficiently such as metals, ceramics, certain polymers and composites. It is important that the acoustic impedance (speed of sound in material multiplied by density of material) be matched so that sound is not reflected from the interface. The intensifier is shaped to match the focus cone of the ultrasound emanating from the piezoelectric element. The fiber or rod may be integral with the intensifier or mechanically removable. Most preferably, the fiber or rod is made of the same material as the intensifier.

Ideally, the diameter of the fiber or rod 19 should be slightly larger than the ultrasound beam size focused at the narrow cross section. Generally, the beam size is related to the width of the piezoelectric element, the focal length determined by the radius of curvature of the element and the wavelength of the sound in the intensifier. The beam size may be estimated by the following formula:

$\theta_{fl}=\lambda/na$ where ha, known as the numerical aperture, is the width (diameter) of the piezoelectric element divided by the focal length.

By way of example, if na=1 and the frequency is 2 Mhz and the guide rod is steel, the beam size will be 3.0 mm in diameter.

One of the main objectives of this invention is to transmit ultrasound over a long distance. The fiber or rod diameters should be as small as possible, consistent with the condition of bulk wave propagation. It is assumed that bulk waves propagate when the diameter is at least one wavelength. Table I provides the preferred fiber or rod diameters for various materials as a function of frequency. Ideally, the diameter should also correspond to the focal point diameter which is $\lambda$/na.

TABLE I

Preferred diameters (corresponding to one wavelength–achievable when na = 1) of various selected rod/fiber materials as functions of selected frequencies.

PREFERRED DIAMETER (mm)
(as a function of active transducer frequency)

TABLE I-continued

| | FREQUENCY (Mhz) | | | | | | | |
|---|---|---|---|---|---|---|---|---|
| ROD/FIBER | 0.5 | 1.0 | 2.0 | 5.0 | 10.0 | 20.0 | 50 | 100 |
| POLY-STYRENE | 4.5 | 2.5 | 1.25 | 0.5 | 0.25 | 0.125 | 0.05 | 0.025 |
| STEEL | 12.0 | 6.0 | 3.0 | 1.2 | 0.6 | 0.3 | 0.12 | 0.06 |
| FUSED SILICA | 12.0 | 6.0 | 3.0 | 1.2 | 0.6 | 0.3 | 0.12 | 0.06 |
| SAPPHIRE | 21.0 | 10.5 | 5.2 | 2.1 | 1.05 | 0.52 | 0.21 | 0.10 |

The configuration of the piezoelectric element having convex and concave faces is such as to cause the emitted ultrasound to propagate down the fiber or rod. The shorter the focus, the higher the intensity at the focal point. Intensity is not the only desired criteria, however. A well-defined sonic pulse shape is also desired. The maximum acoustic pressure point of a given transducer in the compression mode is $P_{max}=D^2/4\lambda$. $P_{max}$ is the distance in front of a planar transducer producing the maximum acoustical pressure. For a spherical piezoelectric element, the focus will be equal to the radius of curvature R. Hence, it is preferred that the distance between the concave surface and the narrow section of the intensifier be between about R and $D^2/\lambda$.

It is useful to consider the angles of the trajectory of the sound wave along the fiber or rod. When the sound wave moves out the distal end of the fiber or rod into the subject to which ultrasound is being applied, the waves are bent outward if the speed of sound is less in the fiber or rod and inward if the speed of sound is greater. The bending is according to Snell's law; namely, $\sin\theta_1/\sin\theta_2=v_1/v_2$ wherein $v_1$ and $v_2$ are the respective velocities of sound in the rod and the subject. Thus, the closer trajectory of the sound waves are to the axis of the rod, the less the bending outward due to the phenomena defined by Snell's law. Table II illustrates this phenomena.

TABLE II

| EXIT ANGLE FROM THE ROD (°) | REFRACTION ANGLE (as a function of material of propagation) (°) | | | |
|---|---|---|---|---|
| | STEEL | DENSE CERAMIC | GREEN CERAMIC | TISSUE |
| POLYSTYRENE ROD/FIBER | | | | |
| 5 | 13 | 23 | 3 | 3 |
| 10 | 27 | 50 | 6 | 7 |
| 30 | — | — | 18 | 19 |
| FUSED SILICA ROD/FIBER | | | | |
| 5 | 5 | 8 | 1 | 1 |
| 10 | 10 | 17 | 2.5 | 2.5 |
| 30 | 10 | 57 | 6.5 | 6.5 |
| SAPPHIRE ROD/FIBER | | | | |
| 5 | 3 | 5 | <1 | <1 |
| 10 | 6 | 10 | 1.5 | 1.5 |
| 30 | 17 | 30 | 4 | 4 |

It ifs also desired that the acoustic impedance mismatch between the fiber or rod and the ambient fluid (e.g., air or body fluid) be very high in order to allow total internal reflections within the fiber or rod itself. When the fiber or rod is made of very high acoustic impedance materials such as steel, fused silica, and sapphire, for example, the mismatch is already very great with respect to air and most other fluids. However, when the fiber or rod is composed of plastic, slight losses would be expected. When low acoustic impedance fibers or rods are used, it is possible to increase the reflection by coating them with metallic layers.

As used in the claims the term "cylindrical" has the generic meaning; namely, of a surface traced by a line intersecting a fixed planar and closed curve. It contemplates a circular cylindrical surface (defining a rod) in which the closed curve is a circle and the line (generatrix) is a straight line as well as other surfaces defining a long narrow rigid or flexible solid with a substantially uniform cross section perpendicular to the longitudinal axis thereof.

Having thus defined my invention with the detail and particularity required by the Patent Laws, what is claimed to be protected by Letters Patent is set forth in the following claims:

1. An ultrasound source for transmitting ultrasound vibrations along a fiber or rod comprising:

a thin piezoelectric element having two closely spaced apart surfaces and having electrodes on each face, one of said faces forming a concave surface and the other a convex surface;

a damping substrate abutting the convex surface;

an acoustic intensifier abutting the concave surface, said acoustic intensifier tapering from the concave surface to a narrow cross section; and a cylindrical fiber or rod extending from said acoustic intensifier at the narrow cross section, the smallest distance across any section of the cylindrical fiber or rod being greater than one and less than five wavelengths of the ultrasound vibrations generated by the piezoelectric element.

2. The ultrasound source according to claim 1 in which the intensifier and cylindrical fiber or rod meet in the vicinity where the ultrasound vibrations are focused.

3. The ultrasound source according to claim 2 in which the focal length of the piezoelectric element and intensifier is between about R and about $D^2/4\lambda$ where R is the radius of curvature of the concave surface of the piezoelectric element near its geometric center, D is the average length cord across the concave surface of the piezoelectric element and $\lambda$ is the wavelength of the ultrasound vibrations generated by the piezoelectric element.

4. The ultrasound source according to claim 3 wherein the concave surface has a circular edge and a radius of curvature that does not vary more than about 20 percent over the entire surface.

5. The ultrasound source according to claim 4 wherein the acoustical intensifier has a conical surface tapering from the circular edge of the concave surface to the narrow cross section, the cylindrical rod or fiber being a circular cylindrical rod or fiber extending from said cross section.

6. The ultrasound source according to claim 5 wherein the diameter of the circular cylindrical fiber or rod is between one and three wavelengths of the ultrasound vibrations generated by the piezoelectric element.

7. The ultrasound source according to claim 1 in which the intensifier occupies a solid angle between $\pi$ and $\pi/2$ steradians.

8. The ultrasound source according to claim 1 in which the maximum angle between a line on the tapered surface of the intensifier and the axis of the cylindrical fiber or rod is between $\pi/3$ and $\pi/6$ radians.

9. The ultrasound source according to claim 1 in which the concave surface of the piezoelectric element is substantially spherical and has a substantially circular edge, and in which the acoustical intensifier has a conical surface tapering from the circular edge to the narrow cross section from which a circular cylindrical fiber or rod extends.

10. The ultrasound source according to claim 1, said acoustical intensifier and the fiber or rod having a sound reflective coating.

11. The ultrasound source according to claim 1 in which the concave surface is spherical or parabolic.

* * * * *

UNITED STATES PATENT AND TRADEMARK OFFICE

CERTIFICATE OF CORRECTION

PATENT NO. : 5,371,483

DATED : December 6, 1994

INVENTOR(S) : Mahesh C. Bhardwaj

It is certified that error appears in the above-indentified patent and that said Letters Patent is hereby corrected as shown below:

Column 1 Line 60 "ill" should read --in--.

Column 3 Line 47 "where ha," should read --where na,--.

Column 4 Line 60 "ifs" should read --is--.

Claim 3 Line 2 Column 6 "length cord" should read --cord length--.

Signed and Sealed this

Twenty-eight Day of March, 1995

Attest:

Bruce Lehman

BRUCE LEHMAN

*Attesting Officer*

*Commissioner of Patents and Trademarks*